(12) United States Patent
White (10) Patent No.: US 8,002,738 B2
(45) Date of Patent: Aug. 23, 2011

(54) SELF-ADHERING LESION FORMATION APPARATUS AND METHODS

(75) Inventor: Brad R. White, Sunnyvale, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1833 days.

(21) Appl. No.: 11/131,012

(22) Filed: May 17, 2005

(65) Prior Publication Data

US 2006/0263418 A1 Nov. 23, 2006

(51) Int. Cl.
*A61M 31/00* (2006.01)
*A61B 17/20* (2006.01)

(52) U.S. Cl. ........................................ 604/93.01; 604/22

(58) Field of Classification Search ............... 604/264, 604/507, 116, 48, 304, 22, 93.01, 285; 424/443, 424/447, 449
See application file for complete search history.

(56) References Cited

U.S. PATENT DOCUMENTS

| | | | |
|---|---|---|---|
| 5,476,664 A * | 12/1995 | Robinson et al. | 424/443 |
| 6,319,467 B1 * | 11/2001 | McLernon, III | 422/58 |
| 6,726,923 B2 | 4/2004 | Iyer et al. | |
| 2002/0037919 A1 | 3/2002 | Hunter | |
| 2003/0073979 A1 | 4/2003 | Naimark et al. | |
| 2003/0195527 A1 | 10/2003 | Helmus | |
| 2004/0013702 A1 | 1/2004 | Glover | |
| 2004/0151764 A1 | 8/2004 | Zamora | |
| 2005/0106206 A1 | 5/2005 | Herweck et al. | |
| 2005/0182390 A1 | 8/2005 | Shanley | |

FOREIGN PATENT DOCUMENTS

WO WO 01/10350 A1 2/2001

\* cited by examiner

*Primary Examiner* — Nicholas D Lucchesi
*Assistant Examiner* — Brooke Matney
(74) *Attorney, Agent, or Firm* — Hendricks, Slavin & Holmes LLP (57) ABSTRACT

A lesion formation apparatus including adhesive and cytotoxic material and methods associated with the same.

14 Claims, 5 Drawing Sheets

SELF-ADHERING LESION FORMATION APPARATUS AND METHODS

BACKGROUND OF THE INVENTIONS

1. Field of Inventions

The present inventions relate generally to the formation of therapeutic lesions in body tissue.

2. Description of the Related Art

There are many instances where therapeutic lesions are formed in body tissue. One conventional method of forming lesions involves the application of electromagnetic radio frequency ("RF") energy to heat and eventually kill (i.e. "ablate") tissue. The ablation energy is typically supplied and controlled by an electrosurgical unit ("ESU") during the therapeutic procedure. More specifically, after an electrophysiology or electrosurgical device has been connected to the ESU, and the electrodes or other energy transmission elements on the device have been positioned adjacent to the target tissue, energy from the ESU is transmitted through the electrodes to the tissue to from a lesion. The amount of power required to coagulate tissue ranges from 5 to 150 W.

With respect to the formation of therapeutic lesions in heart tissue to treat cardiac conditions such as atrial fibrillation, atrial flutter and arrhythmia, some procedures utilize electrode-carrying catheters which form lesions on the endocardium in order to create a maze for electrical conduction similar to that created by surgical maze procedures. The lesions are carefully placed to interrupt the conduction routes of the most common reentry circuits. Exemplary catheters are disclosed in U.S. Pat. Nos. 6,013,052, 6,203,525, 6,214,002 and 6,241,754. Surgical soft tissue coagulation probes that carry one or more electrodes on relatively short, stiff shafts have also been used in endocardial and epicardial procedures where access to the heart is obtained by way of a thoracostomy, thoracotomy or median sternotomy. Exemplary surgical probes are disclosed in U.S. Pat. Nos. 6,142,994, 6,468,272 and 6,645,200. Electrosurgical clamps have also been used to form lesions around, for example, a pairs of pulmonary veins. Exemplary electrosurgical clamps are disclosed in U.S. Pat. No. 6,142,994 and U.S. Pat. App. Pub. No. 2003/0158547.

One of the advantages associated with electrophysiological and electrosurgical procedures is the rapid nature of the lesion formation after the electrodes have been positioned against the target tissue. Typically, an irreversible transmural lesion will be formed in heart tissue within a few seconds after the energy transmission process is initiated. The present inventor has, however, determined that there may be some instances where the rapid formation of irreversible lesions is undesirable.

SUMMARY OF THE INVENTIONS

A lesion formation method in accordance with one embodiment of a present invention includes the step of adhering a lesion formation apparatus including a therapeutically effective amount of a cytotoxic agent to an epicardial surface. A lesion formation apparatus in accordance with one embodiment of a present invention includes a relatively long, thin backing, a pressure sensitive adhesive and a therapeutically effective amount of a cytotoxic material located along the majority of the length of the backing.

Such methods and apparatus provide a number of advantages over conventional methods and apparatus. For example, the cytotoxic agent may be one which will not do any more than superficial damage to tissue for a period sufficient to provide the physician with enough time to position a lesion formation apparatus on the target tissue structure, observe the lesion formation apparatus, and move the lesion formation apparatus if necessary. The inventions are especially useful in the context of forming complex lesion patterns because they allow the physician to form the entire pattern on tissue and adjust it, if necessary, before any of the lesions are formed.

A lesion formation assembly in accordance with one embodiment of a present invention includes a carrier and one or more lesion formation apparatus with a backing, a pressure sensitive adhesive and a therapeutically effective amount of a cytotoxic material located along the majority of the length of the backing. Such an assembly provides a number of advantages. For example, the assembly may include a plurality of lesion formation apparatus that are configured to be arranged in a pattern that will produce a predetermined curative lesion pattern.

The above described and many other features and attendant advantages of the present inventions will become apparent as the inventions become better understood by reference to the following detailed description when considered in conjunction with the accompanying drawings.

BRIEF DESCRIPTION OF THE DRAWINGS

Detailed description of preferred embodiments of the inventions will be made with reference to the accompanying drawings.

DETAILED DESCRIPTION OF THE PREFERRED EMBODIMENTS

The following is a detailed description of the best presently known modes of carrying out the inventions. This description is not to be taken in a limiting sense, but is made merely for the purpose of illustrating the general principles of the inventions.

The detailed description of the preferred embodiments is organized as follows:

I. Introduction
II. Exemplary Lesion Formation Apparatus And Assemblies
III. Exemplary Methods
IV. Exemplary Lesion Formation Kits The section titles and overall organization of the present detailed description are for the purpose of convenience only and are not intended to limit the present inventions.

I. Introduction

This specification discloses a number of structures, mainly in the context of cardiac treatment, because the structures are well suited for use with myocardial tissue and arrhythmia conditions within the heart. Nevertheless, it should be appreciated that the structures are applicable for use in therapies involving other types of soft tissue. For example, various aspects of the present inventions have application in pain treatment procedures.

II. Exemplary Lesion Formation Apparatus and Assemblies

Figure 1:
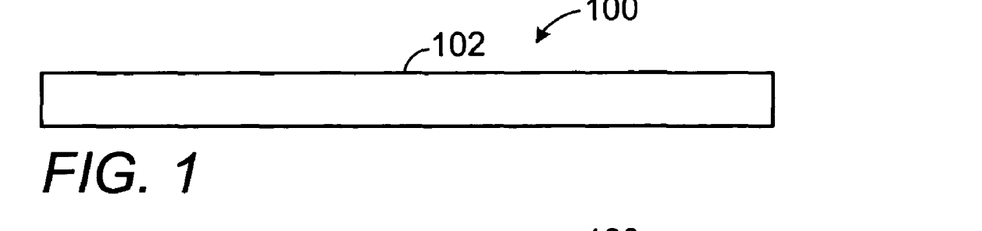
FIG. 1 is a plan view of a lesion formation apparatus in accordance with one embodiment of a present invention.
Figure 2:
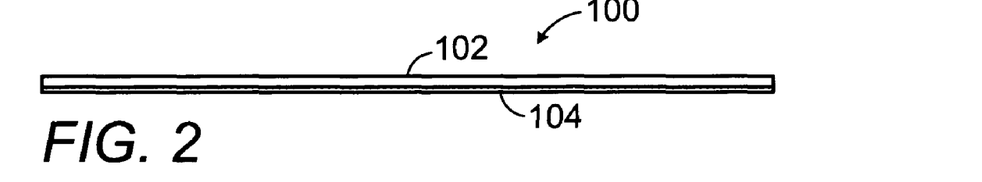
FIG. 2 is a side view of the lesion formation apparatus illustrated in FIG. 1.
Figures 3, 4:
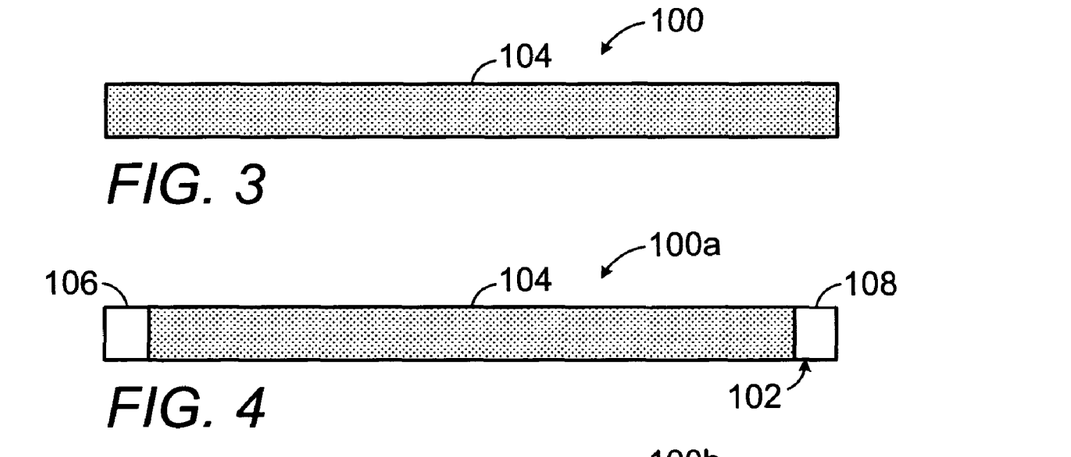
FIG. 3 is a bottom view of the lesion formation apparatus illustrated in FIG. 1.
FIG. 4 is a bottom view of a lesion formation apparatus in accordance with one embodiment of a present invention.

As illustrated for example in FIGS. 1-3, a lesion formation apparatus 100 in accordance with one embodiment of a present invention includes a backing 102 and a layer of adhesive doped with a therapeutically effective amount of a cytotoxic agent ("cytotoxic adhesive") 104 that coats the surface of the backing. The lesion formation apparatus 100 may be placed in contact with a target tissue surface and will remain adhered to the tissue surface until removed by the physician.

Suitable cytotoxic agents include chemotherapeutic agents such as paclitaxol and other cytotoxins used in chemical ablation. Preferably, the selected cytotoxic agent will be one that will not do any more than superficial damage to tissue for at least 20-30 minutes in order to provide the physician with enough time position one or more of the lesion formation apparatus 100 on the target tissue structure, observe the lesion formation apparatus, and move the lesion formation apparatus if necessary. As used herein, "a therapeutically effective amount" of a cytotoxic agent means that the concentration or quantity of the cytotoxic agent is high enough to kill the target tissue through diffusion without producing unacceptable toxic symptoms in other regions of the body. In the context of atrial tissue, for example, a therapeutically effective amount would be an LD 90 dose (i.e. a dose that, when applied topically, kills 90% of the cells) that is effective up to 5 mm from the point of application. Killing 90% of the cells renders the tissue electrically disconnected from adjacent cells, and the atrial wall is typically no more than 5 mm thick.

The backing 102 may be an suitable material that is capable of carrying the cytotoxic adhesive 104 and conforming to the shape of the target tissue structure. The backing material should also be configured to prevent the cytotoxic agent leeching though the backing 102 to the side of the backing opposite the cytotoxic adhesive 104. One exemplary backing material is nonperforated ethylene vinyl acetate. In some instances, it may be desirable to use bio-resorbable backing material, such as polylactic acid (PLA) or polyglycolic acid (PGA), that will dissolve and assimilate into the body after the cytotoxic agent has formed a curative lesion in the target tissue (typically about 4-10 hours).

With respect to the adhesive, suitable adhesives include pressure sensitive adhesives such as pressure sensitive acrylate adhesives and other polymer based pressure sensitive adhesives. The adhesive should be removable immediately or after the time period required for the cytotoxic agent to form the therapeutic lesion. In some instances, it may also be desirable to employ adhesives that will dissolve after the cytotoxic agent has formed a curative lesion in the target tissue. Adhesives used in the area of wound closure are suitable examples of dissolvable adhesives.

The lesion formation apparatus illustrated in FIGS. 1-3 may be modified in a variety of ways. Referring to FIG. 4, the exemplary lesion formation apparatus 100a is configured such that the cytotoxic adhesive 104 does not cover the entire surface of the backing 102, as it does in the lesion formation apparatus illustrated in FIGS. 1-3. The lack of cytotoxic adhesive 104 at the longitudinal ends of the backing 102 creates backing tabs 106 and 108 that will not adhere to tissue and may be gripped during the application, repositioning and/or removal processes.

Figure 5:
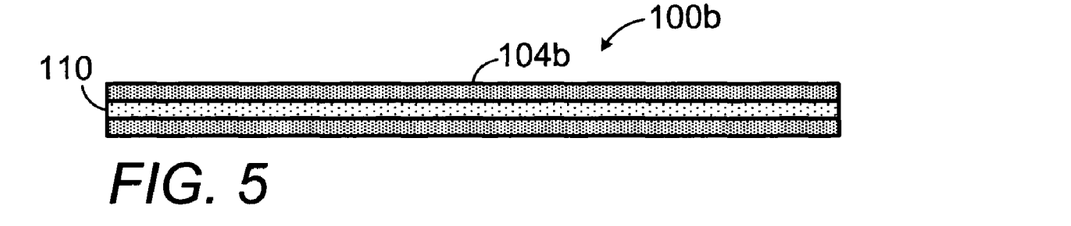
FIG. 5 is a bottom view of a lesion formation apparatus in accordance with one embodiment of a present invention.
Figure 6:
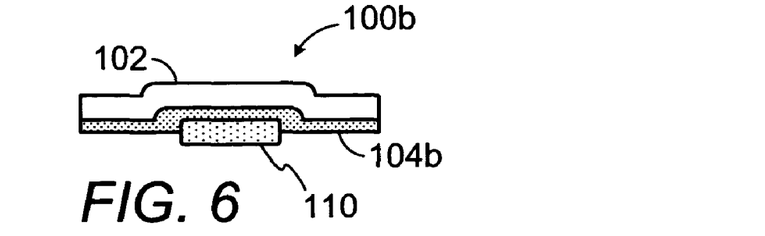
FIG. 6 is an end view of the lesion formation apparatus illustrated in FIG. 5.

Another exemplary lesion formation apparatus is generally represented by reference numeral 100b in FIGS. 5 and 6. The pressure sensitive adhesive 104b is not doped with a cytotoxic agent. Instead, the lesion formation apparatus 100b includes a polymer rod 110 that is doped with (or coated by) the cytotoxic agent. The exemplary cytotoxic rod 110 extends the length of the backing 102 and is held in place by the adhesive 104b. The cytotoxic rod 110 may be shorter than the backing 102, or longer, if applications so require. The cytotoxic rod 110 is also narrower than the backing 102. The adhesive 104b will, therefore, be exposed on opposite sides of the cytotoxic rod 110 along the length of the backing 102 so that the adhesive will be able to hold the backing, and cytotoxic rod, firmly against the tissue. Additionally, and referring more specifically to FIG. 6, the cytotoxic rod 110 also extends downwardly (in the illustrated orientation) beyond the adhesive. This arrangement insures that there will be proper rod/tissue contact when the lesion formation apparatus 100b is secured to a tissue structure.

Although the exemplary cytotoxic rod 110 has a cross-sectional shape that is generally flat and rectangular (FIG. 6), other shapes may be employed. For example, cytotoxic rods that have circular, rectangular, elliptical or any other suitable cross-sectional shape may also be employed.

Figures 7, 8:
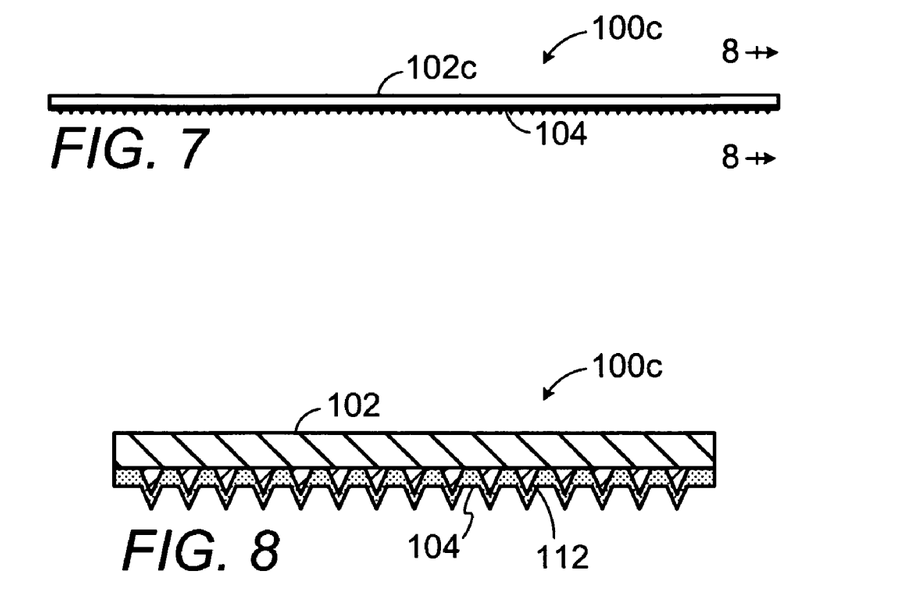
FIG. 7 is a side view of a lesion formation apparatus in accordance with one embodiment of a present invention.
FIG. 8 is a section view taken along line 8-8 in FIG. 7.

Turning to FIGS. 7 and 8, the exemplary lesion formation apparatus 100c illustrated therein is particularly applicable to situations where it is difficult for the cytotoxic agent in the adhesive to penetrate the tissue structure. To that end, the lesion formation apparatus 100c is provided with a penetration enhancer in the form of a plurality of small piercing needles 112. The piercing needles 112, as well as the spaces between the needles, are covered by the cytotoxic adhesive 104. As a result, when the lesion formation apparatus 100c is adhered to a target tissue structure, the cytotoxic agent will be in contact with tissue on the surface of the structure as well as tissue below the surface. The size and spacing of the piercing needles will depend on the intended procedure. In the case epicardial procedures such as those discussed below with reference to FIGS. 14A-14C, a suitable piercing needle arrangement would include piercing needles 112 that are about 1 mm to 3 mm long and about 0.1 mm to 0.2 mm in diameter with a spacing of about 1 mm to 3 mm between adjacent needles.

The piercing needles 112 may be incorporated into the lesion formation apparatus in a variety of ways. In the exemplary embodiment, the piercing needles 112 are formed on the backing 102 using a screen printing or other suitable deposition process. The piercing needles 112 may, alternatively, be formed as part of a bio-resorbable molded strip that is secured to a bio-resorbable backing. Preferably, the strip will dissolve after the lesion has been formed, but prior to the backing. It should be noted that other penetration enhancers, such as chemical penetration enhancers (e.g. dimethylsulfoxide), may be employed in place of needles and other structural penetration enhancers. Piercing needles and/or other structural penetration enhancers, and/or chemical penetration enhancers may also be incorporated into the cytotoxic rod 110.

Lesion formation apparatus in accordance with the present inventions may also be provided with structures that improve the physician's ability to precisely determine the location of the lesion formation apparatus relative to the target tissue structure. As illustrated for example in FIG. 9, the lesion formation apparatus 100d includes a visible marker 114 on the backing 102. Such a visible marker 114 may be configured to be directly visible to the physician during a therapeutic procedure by, for example, locating the visible marker on the top surface of the backing 102 (i.e. the surface opposite the cytotoxic adhesive 104) and making the visible marker and the backing different colors. Another alternative is to omit the marker 114 and simply form the backing 102 from material of a color (e.g. white or light green) that will stand out during the therapeutic procedure. Alternatively, or additionally, the visible marker 114 may be formed from a flexible strip of radiopaque material so that it may be observed through the use of fluoroscopy or other suitable imaging techniques.

Figure 9:
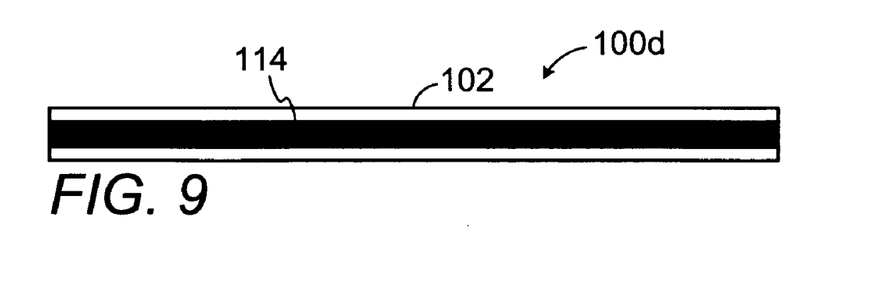
FIG. 9 is a plan view of a lesion formation apparatus in accordance with one embodiment of a present invention.

Tactile visibility may be employed as an alternative to, or in addition to, the optical and radiographic visibility described above. For example, the surface of the backing 102 (or the marker 114, if present) may be roughened so that the physician will be able to use his/her fingers to tactilely observe a lesion formation apparatus that is on the back side of the target organ, relative to the physician's location, or is otherwise out of the line of sight.

Figure 10:
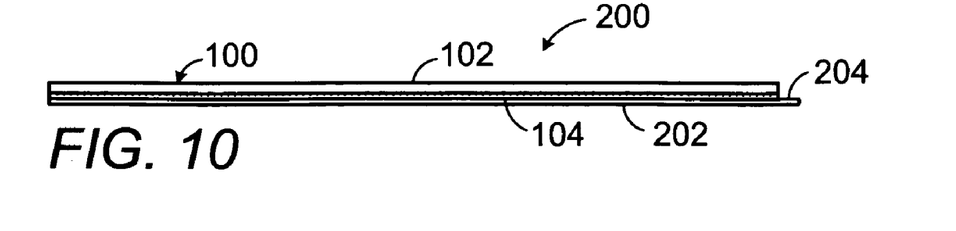
FIG. 10 is a side view of a lesion formation assembly in accordance with one embodiment of a present invention.

Turning to FIG. 10, an exemplary lesion formation assembly 200 the lesion formation apparatus 100 (or one the apparatus 100a-100d) on a carrier 202. Suitable carriers include, for example, non-stick polymer liners treated on one side with silicone. The silicone treatment allows the lesion formation apparatus 100 to be readily removed from the carrier 202 during the therapeutic procedure. With respect to removal, the exemplary carrier 202 includes a tab 204 that extends beyond the longitudinal end of the lesion formation apparatus 100. The tab 204 facilitates the peeling of the lesion formation apparatus 100 from the carrier 202.

Figure 11:
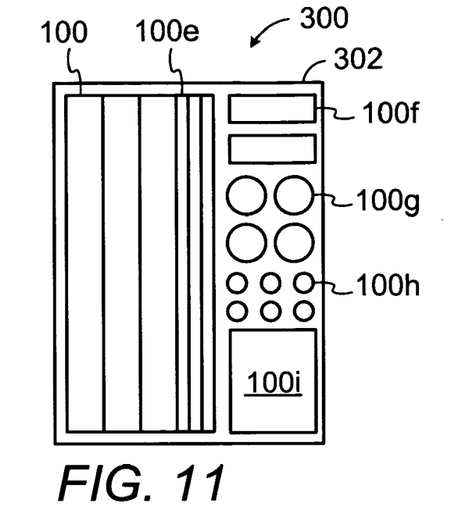
FIG. 11 is a plan view of a lesion formation assembly in accordance with one embodiment of a present invention.

Another exemplary lesion formation assembly is generally represented by reference numeral 300 in FIG. 11. The carrier 302, which is structurally similar to the carrier 202, carries a plurality of the lesion formation apparatus 100 (or the apparatus 100a-100d) as well as other lesion formation apparatus 100e-100i. The lesion formation apparatus 100e-100i are differently shaped than the lesion formation apparatus 100, but are otherwise structurally similar to one or more of the lesion formation apparatus 100-100d. As a result, the lesion formation assembly 300 provides the physician with the ability to select from a number of different lesion formation apparatus for one that is most suitable for the intended target tissue.

Figure 12:
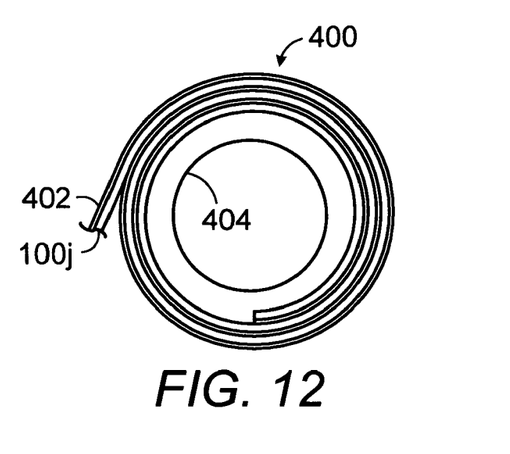
FIG. 12 is a side view of a lesion formation assembly in accordance with one embodiment of a present invention.

Lesion formation apparatus in accordance with the present inventions may also be stored in roll form. Referring more specifically to FIG. 12, the exemplary lesion formation assembly 400 includes an elongate lesion formation apparatus 100j and an elongate carrier 402 rolled around a base member 404. Such a storage technique allows varying lengths of the lesion formation apparatus 100j to be unrolled and severed from the remainder of the roll. The elongate lesion formation apparatus 100j may be otherwise structurally similar to the any of the lesion formation apparatus 100-100e.

The shape and dimensions of lesion formation apparatus will, of course, depend on the intended application. In the exemplary context of epicardial lesion formation, the lesion formation apparatus will typically be relatively long and thin, i.e. the length-to-width ratio will be about 5 to 1 or greater. For example, the lesion formation apparatus may be about 1 mm to 2 mm wide and at least about 1 cm in length or longer.

III. Exemplary Methods

Figure 13:
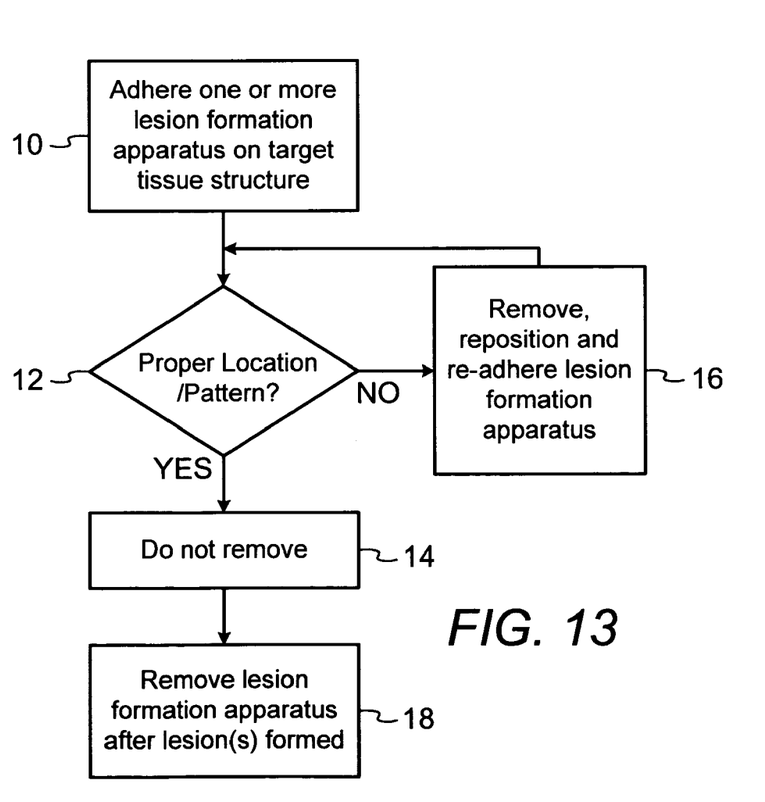
FIG. 13 is a flow chart illustrating a method in accordance with one embodiment of a present invention.

The lesion formation apparatus and assemblies described above may be used in a variety of therapeutic procedures. Referring to FIG. 13, a method in accordance with one of the present inventions includes the steps of adhering one or more of the lesion formation apparatus 100 to the target organ or other tissue structure (Step 10). In those instances where a plurality of lesion formation apparatus are employed, the lesion formation apparatus may be arranged in a predetermined pattern corresponding to a particular curative lesion pattern. The lesion formation apparatus do not, as noted above, create lesions instantaneously. Accordingly, the physician will be able to observe the location and/or pattern of the one or more adhered lesion formation apparatus (Step 12). If the location and/or pattern of the one or more adhered lesion formation apparatus is acceptable, the physician will leave the lesion formation apparatus in place for the period (e.g. about 4-10 hours) required to form a curative lesion (Step 14). If the location and/or pattern on the target organ or other tissue structure is not acceptable, then the physician will remove, reposition and re-adhere the lesion formation apparatus (Step 16). The lesion formation apparatus will be removed once the lesion and/or lesion pattern is formed (Step 18).

Figure 14A:
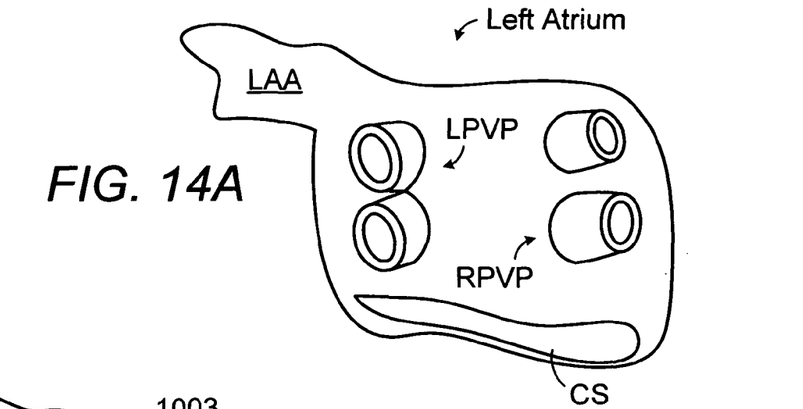
FIGS. 14A-14C are posterior views of the left atrium illustrating a method in accordance with one embodiment of a present invention.

One specific application of the present lesion formation apparatus and assemblies is the formation of transmural lesions in myocardial tissue to cure atrial fibrillation. The transmural lesions are formed in a curative pattern on the epicardial surface of the left atrium by adhering a plurality of lesion formation apparatus thereto. To that end, and as illustrated in FIG. 14A, the left atrial structures which are relevant to the following discussion include the right pulmonary vein pair ("RPVP"), the left pulmonary vein pair ("LPVP"), the coronary sinus ("CS") and the left atrial appendage ("LM"). The curative pattern includes one, some or all of the following lesions—a lesion around the RPVP, a lesion around the LPVP, a lesion connecting the lesions around the RPVP and LPVP, a lesion that extends from one of the lesions around the RPVP and LPVP to the CS, a lesion around the LAA and, in those instances where the lesions around the LPVP and the LAA do not overlap, a lesion that connects the lesions around the LPVP and the LM.

Figure 14B:
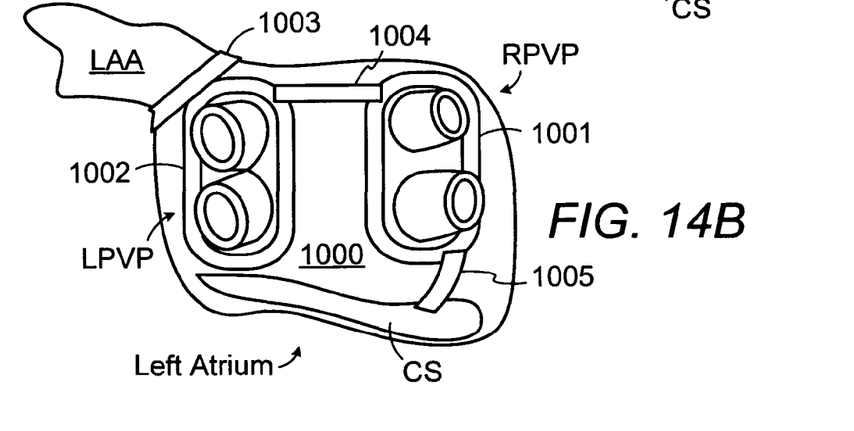

The plurality of lesion formation apparatus illustrated in FIG. 14B have been adhered to the epicardial surface in a pattern 1000 that will form the atrial fibrillation curing lesion pattern described above. Additionally, it should be noted that although the discussion below refers to the lesion formation apparatus 100, the lesion formation apparatus 100a-f and 100j could also be employed. The pattern 1000 could also include more than one type lesion formation apparatus (e.g. one or more of the lesion formation 100 and one or more of the lesion formation apparatus 100c) if necessary.

The pattern 1000 includes a pattern portion 1001, which may be formed by one or more of the lesion formation apparatus 100, extending continuously around the RPVP. There is also a pattern portion 1002, which may be formed by one or more of the lesion formation apparatus 100, extending continuously around the LPVP. A pattern portion 1003, which may be formed by one or more of the lesion formation apparatus 100, extends continuously around the LAA. A pattern portion 1004, which may be formed by one of the lesion formation apparatus 100, connects the pattern portion 1001 around the RPVP to the pattern portion 1002 around the LPVP. A pattern portion 1005, which may be formed by one of the lesion formation apparatus 100, connects either the pattern portion 1001, or the pattern portion 1002, to the CS.

The above-described pattern 1000 may be modified in a variety of ways. For example, pattern portion 1004 may be eliminated and pattern portions 1001 and 1002 may be enlarged to the extent that they overlap. Pattern portions 1002 and 1004 may, alternatively, be eliminated and pattern portion 1001 may be enlarged to the extent that it surrounds all four pulmonary veins. Pattern portions 1001 and 1002 may also be eliminated and replaced by four pattern portions that individually surround the four pulmonary veins.

Once the lesion formation apparatus 100 which make up the various pattern portions 1001-1005 have been adhered to the epicardial surface, the physician will be able to observe the pattern 1000 to determine whether or not any of the pattern portions require repositioning. If the pattern 1000 is acceptable, the physician will leave the pattern portions 1001-1005 in place for the period (e.g. about 4-10 hours) required for the formation of a curative lesions. If not, the physician will remove, reposition and re-adhere the some or all of the lesion formation apparatus 100 that make up the pattern portions 1001-1005, and then leave them in place for the required period.

Figure 14C:
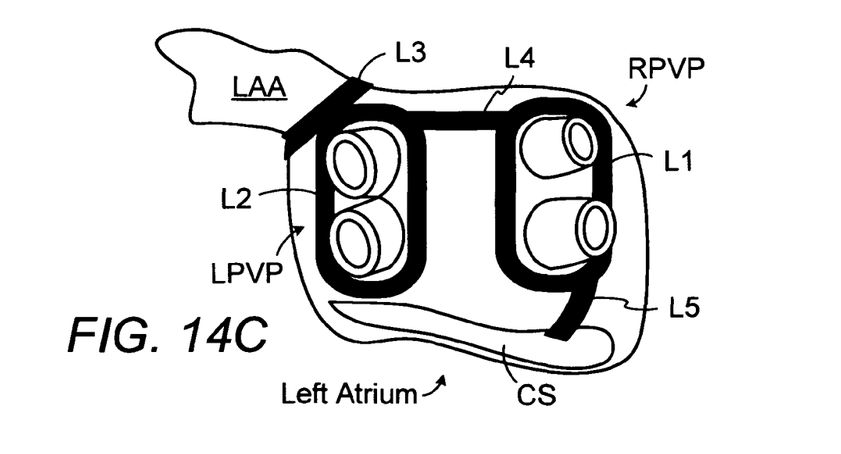

The adhered lesion formation apparatus 100 which make up the various pattern portions 1001-1005 will be removed from the epicardial surface at the end of the required period in order to reveal the transmural lesions formed by the cytotoxic agent in the adhesive or rod. Turning to FIG. 14C, the lesion pattern formed by the lesion formation apparatus pattern illustrated in FIG. 14B includes a continuous transmural lesion L1 that extends completely around the RPVP, a continuous transmural lesion L2 that extends completely around the LPVP, and a continuous transmural lesion L3 that extends completely around the LAA and overlaps a portion of lesion L2. There is also a continuous transmural lesion L4 that connects lesions L1 and L2 as well as a continuous transmural lesion L5 that extends from lesion L1 to the CS.

A similar procedure may be used to form curative lesions in the epicardial surface of the right atria. Here, for example, the curative pattern may include a first transmural lesion that extends from the superior vena cava, along the crista terminalis to the atrioventricular (AV) groove, and a second transmural lesion that extends from the inferior vena cava up to and crossing the first lesion near the AV groove. The lesion formation apparatus pattern formed by one or more of the lesion formation apparatus 100 would, therefore, include a first pattern portion that extends from the superior vena cava, along the crista terminalis to the atrioventricular (AV) groove, and a second pattern portion that extends from the inferior vena cava up to and crossing the pattern portion near the AV groove.

Other methods in accordance with the present inventions are associated with the treatment of chronic pain due to disease or injury. Here, one or more of the lesion formation apparatus could be positioned proximate the pain initiating area and used to kill the endings of the nerves that are generating the pain signals.

IV. Exemplary Lesion Formation Kits

Figure 15:
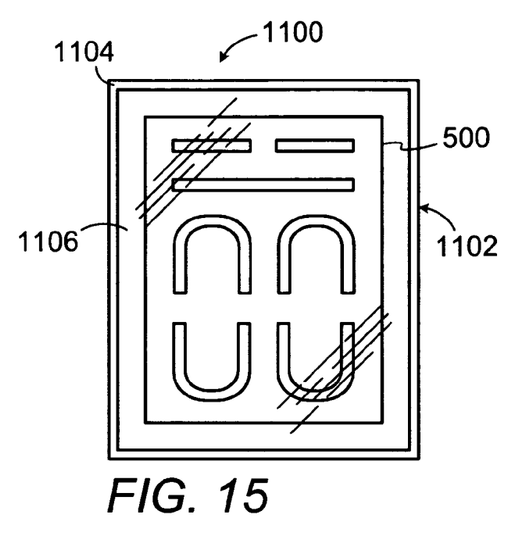
FIG. 15 is a plan view of a lesion formation kit in accordance with one embodiment of a present invention.

The present inventions also include lesion formation kits. As illustrated for example in FIG. 15, a lesion formation kit 1100 in accordance with one embodiment of a present invention includes a container 1102 and a lesion formation assembly within the container. The container 1102 is preferably a sterile package that has a flat, relatively rigid bottom portion 1104 and a top transparent top cover 1106 that allows the lesion formation assembly to be viewed. The lesion formation assembly may include a plurality of lesion formation apparatus 100-100i, from which the physician can pick and choose, that are stored either in individual form (i.e. a plurality lesion formation assemblies that each includes a single lesion formation apparatus) or in group form (i.e. a lesion formation assembly with a plurality of lesion formation apparatus).

The lesion formation assembly in such a kit may also be configured to perform a specific therapeutic procedure. The exemplary lesion formation kit 1100 illustrated in FIG. 15 includes a lesion formation assembly 500 with a carrier 502 and a plurality of individual lesion formation apparatus that together are configured to create the lesion formation apparatus pattern 1000 illustrated in FIG. 14B. The lesion formation apparatus may be one or more the lesion formation apparatus 100-100f illustrated in FIGS. 1-9 and 11. As noted above, the lesion formation apparatus pattern 1000 will form the lesion pattern illustrated in FIG. 14C to cure atrial fibrillation.

Figure 16:
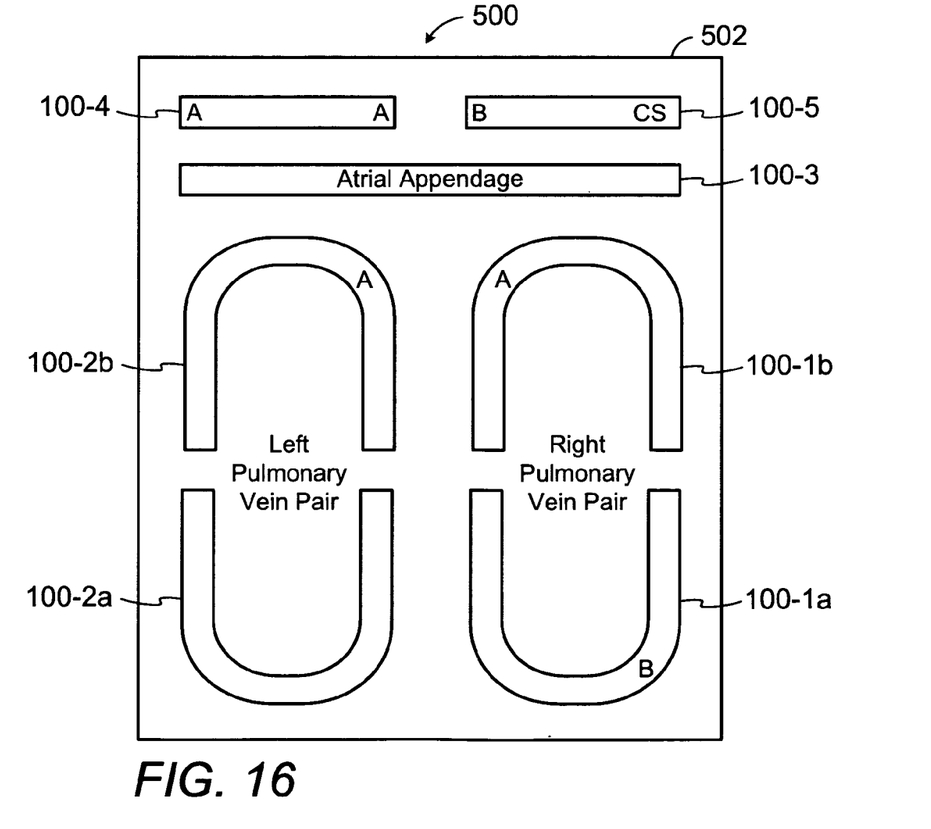
FIG. 16 is a plan view of a lesion formation assembly in accordance with one embodiment of a present invention.

Referring more specifically to FIG. 16, the lesion formation assembly 500 includes lesion formation apparatus 100-1a and 100-1b that together form pattern portion 1001, as well as lesion formation apparatus 100-2a and 100-2b that together form pattern portion 1002. Pattern portions 1001 and 1002 each define a closed shape (e.g. oval, circular, rectangular, etc.) that will enclose the associated pulmonary vein pair. Each closed shape is formed from two lesion formation apparatus in order to reduce the difficulty associated with forming such a shape around a pulmonary vein pair. In the illustrated embodiment, the lesion formation apparatus 100-1a and 100-1b are substantially identical and are substantially U-shaped (as are lesion formation apparatus 100-2a and 100-2b) and can be applied to the epicardial surface from opposite sides of the pulmonary vein pair. The lesion formation apparatus 100-1a and 100-1b (as well as the lesion formation apparatus 100-2a and 100-2b) should also be sized in such a manner that the free ends of the U-shapes overlap slightly in order to insure that continuous lesions will be formed.

Figure 17:
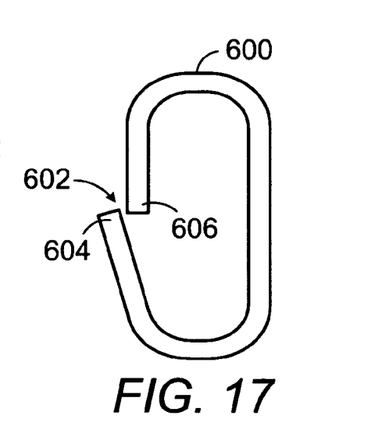
FIG. 17 is a plan view of a lesion formation apparatus in accordance with one embodiment of a present invention.

The pattern portions 1001 and 1002 may also each be formed by a respective single elongate lesion formation apparatus. Such a single lesion formation apparatus may be linear and bent by the physician during the adhesion process. Alternatively, as illustrated in FIG. 17, a lesion formation apparatus 600, which is configured to form pattern portion 1001 (or 1002) around a pulmonary vein pair, is precut in an overall closed shape with a slit 602 that allows the apparatus to be positioned around the pulmonary vein pair. The exemplary lesion formation apparatus 600 is also configured such that the free ends 604 and 606 can be overlapped slightly when the apparatus is adhered to the epicardial surface in the manner illustrated in FIG. 14B.

Turning to the other portions of the lesion formation apparatus pattern 1000 created with the exemplary lesion formation assembly 500 illustrated in FIG. 16, the assembly also includes lesion formation apparatus 100-3, which is sized and shaped to be adhered to the epicardial surface around the LM and form pattern portion 1003 (FIG. 14B), lesion formation apparatus 100-4, which is sized and shaped to form pattern portion 1004, and lesion formation apparatus 100-5, which is sized and shaped to form pattern portion 1005.

Lesion formation assemblies in accordance with the present inventions may also be provided with indicia that facilitates the intended use of the lesion formation apparatus therein. Such indicia may, for example, be used to provide information concerning the lesion formation apparatus in the particular assembly and/or the pattern that the lesion formation apparatus are intended to form. The indicia may be provided on the carrier 502 and/or on one or more of the lesion formation apparatus. Referring to FIG. 16, the exemplary lesion formation assembly 500 includes indicia (i.e. "right pulmonary vein pair," "left pulmonary vein pair," and "atrial appendage") that indicates which of the left atrial structures are to be treated with the associated lesion formation apparatus. With respect to the pattern formed by the lesion formation apparatus, indicia may be provided to show where the pattern portions are connected to one another. Such indicia may be in the form of symbols (e.g. letters or numbers), colors or tactile markers. In the illustrated embodiment, the lesion formation apparatus 100-1*b*, 100-2*b* and 100-4 include the letter "A" to show where lesion formation apparatus 100-4 should be connected to the lesion formation apparatus 100-1*b* and 100-2*b*. Lesion formation apparatus 100-1*a* includes the letter "B," as does the lesion formation apparatus 100-5, to show where they are connected to one another. Lesion formation apparatus 100-5 also includes the letters "CS," which indicate that the associated end of the apparatus should be positioned on the coronary sinus.

Although the present inventions have been described in terms of the preferred embodiments above, numerous modifications and/or additions to the above-described preferred embodiments would be readily apparent to one skilled in the art. By way of example, but not limitation, the inventions include any and all combinations of the elements from the various embodiments disclosed in the specification. The present inventions also include lesion formation kits including a container and one or more of the lesion formation apparatus or assemblies described above and/or claimed below. It is intended that the scope of the present inventions extend to all such modifications and/or additions and that the scope of the present inventions is limited solely by the claims set forth below.

I claim:

1. A lesion formation assembly, comprising:
   a carrier; and
   a plurality of lesion formation apparatus carried by the carrier, each lesion formation apparatus including
   a relatively long, thin backing,
   a pressure sensitive adhesive associated with the backing, and
   a therapeutically effective amount of a cytotoxic material in direct contact with the carrier located along at least the majority of the length of the backing.

2. An assembly as claimed in claim 1, wherein at least two of the plurality of lesion formation apparatus define respective sizes and shapes and at least one of the sizes and the shapes are not the same.

3. An assembly as claimed in claim 1, wherein the carrier comprises a non-stick polymer liner.

4. An assembly as claimed in claim 1, wherein the carrier comprises a sheet of liner material.

5. An assembly as claimed in claim 1, wherein the cytotoxic material of each lesion formation apparatus is between the carrier and the backing.

6. A lesion formation assembly, comprising:
   a carrier; and
   a plurality of lesion formation apparatus carried by the carrier, sized and shaped to create a predetermined pattern, and each including
   a relatively long, thin backing,
   a pressure sensitive adhesive associated with the backing, and
   a therapeutically effective amount of a cytotoxic material located along at least the majority of the length of the backing.

7. An assembly as claimed in claim 6, wherein the lesion formation apparatus are configured to form a first closed shape around a first pulmonary vain pair and a second closed shape around a second pulmonary vein pair.

8. An assembly as claimed in claim 6, wherein the predetermined pattern corresponds to a therapeutic epicardial lesion pattern for treating atrial fibrillation.

9. An assembly as claimed in claim 6, wherein at least two of the lesion formation apparatus include indicia that indicates which portions of the at least two lesion formation apparatus are to be connected to one another to form at least a portion of the predetermined pattern.

10. An assembly as claimed in claim 6, wherein the cytotoxic material is in direct contact with the carrier.

11. An assembly as claimed in claim 10, wherein the carrier comprises a non-stick polymer liner.

12. An assembly as claimed in claim 10, wherein the carrier comprises a sheet of liner material.

13. An assembly as claimed in claim 6, wherein the cytotoxic material of each lesion formation apparatus is between the carrier and the backing.

14. An assembly as claimed in claim 6, wherein at least two lesion formation apparatus are secured to one another in the predetermined pattern.

* * * * *